United States Patent [19]

Kampling et al.

[11] Patent Number: 5,101,056
[45] Date of Patent: Mar. 31, 1992

[54] PROCESS FOR CONVERTING AMINO ORGANOSILICON COMPOUNDS TO ACRYLAMIDE ORGANOSILICON COMPOUNDS

[75] Inventors: Matthew J. Kampling, Ypsilanti; Michael A. Lutz, Midland; Kristen A. Scheibert, Sanford, all of Mich.

[73] Assignee: Dow Corning Corporation, Midland, Mich.

[21] Appl. No.: 633,908

[22] Filed: Dec. 26, 1990

[51] Int. Cl.$^5$ ................................................ C07F 7/10
[52] U.S. Cl. ...................................................... 556/419
[58] Field of Search ........................................ 556/419

[56] References Cited

U.S. PATENT DOCUMENTS

| | | | |
|---|---|---|---|
| 2,929,829 | 3/1960 | Morehouse | 260/448.2 |
| 4,152,346 | 5/1979 | Seiler et al. | 260/448.8 R |
| 4,507,455 | 3/1985 | Tanguey et al. | 528/26 |
| 4,608,270 | 8/1986 | Varaprath | 427/35 |
| 4,697,026 | 9/1987 | Lee et al. | 556/419 |
| 4,861,906 | 8/1989 | Varaprath | 556/419 |
| 4,861,907 | 8/1989 | Wright et al. | 556/419 |
| 4,889,942 | 12/1989 | Gutek et al. | 556/419 |
| 4,933,413 | 6/1990 | Varaprath | 556/419 X |

FOREIGN PATENT DOCUMENTS 74113   6/1981   Japan .

*Primary Examiner*—Paul F. Shaver
*Attorney, Agent, or Firm*—Roger H. Borrousch

[57] ABSTRACT

Acrylamide functional siloxanes are made by a method which is an improvement over the method for preparing them by reacting an amino functional siloxane in the presence of a non-aqueous solvent, a metal alkoxide, and a non-aqueous cosolvent for the metal alkoxide. The improvements include using a non-polar solvent, an alcohol cosolvent, cooling a mixture of amino functional siloxane, non-polar solvent, and non-protic acid acceptor before adding the alcohol cosolvent, and neutralizing with a mild base. Conversion of the amino functionality to acrylamide is above 95 percent, the acrylamide has low ionics, and the viscosity of the acrylamide is essentially the same as the viscosity of the starting amino functional siloxane.

6 Claims, No Drawings

PROCESS FOR CONVERTING AMINO ORGANOSILICON COMPOUNDS TO ACRYLAMIDE ORGANOSILICON COMPOUNDS

BACKGROUND OF THE INVENTION

1. Field of the Invention

This invention relates to a method for preparing organosilicon compounds that contain silicon-bonded acrylamide substituted hydrocarbon radicals. More specifically, the method involves the reaction of aminoalkylsiloxanes with acryloyl halides in nonaqueous media and in the presence of metal alkoxides to produce acylamide organosilicon compounds.

2. Background Information

Organosilicon compounds that contain silicon-bonded acylamino-substituted hydrocarbon radicals are well known and have been described in U.S. Pat. No. 4,608,270, issued Aug. 26, 1986 to Varaprath which is herein incorporated by reference.

As mentioned in Varaprath U.S. Pat. No. 4,608,270 and as taught in U.S. Pat. No. 2,929,829, issued Mar. 22, 1960, to Morehouse, Japan 56/74113, published June 19, 1981 to Takamizawa and U.S. Pat. No. 4,152,346, issued May 1, 1979, to Koetzsch et al., acylaminoorganopolysiloxanes can be synthesized by reacting aminosiloxanes with the corresponding acid chloride in the presence of a tertiary amine such as triethylamine. However, such a synthesis has several disadvantages. First, the removal of the voluminous precipitate of triethylamine hydrochloride by filtration is tedious. Second, a small amount of HCl is liberated even when an excess of amine is used. This HCl is detrimental to the stability of the polymer especially when the acid chloride has other reactive vinyl functionality such as where the acid chloride is acrylyl chloride.

An alternative method for the preparation for the acylamino organosilicon compounds involves the reaction of an acid anhydride or ester with aminosiloxanes and silanes at elevated temperature. This is taught in U.S. Pat. No. 4,507,455, issued Mar. 26, 1985, to Tangney and Ziemelis. Unfortunately at the elevated temperatures of the reaction, acrylamide derivatives undergo Michael addition and amidation of the acrylic double bond resulting in unwanted by-products and crosslinkage of the desired product which ultimately causes the polymer to gel.

Further, as taught in U.S. Pat. No. 4,608,270 to Varaprath, these problems can be overcome by reacting the aminosilanes and siloxanes with acid chlorides in the presence of aqueous sodium hydroxide. However, a problem arises from the fact that this reaction is carried out in a two-phase system in which the aminosiloxane is dissolved in an organic solvent that is immiscible with water. The HCl that is produced on addition of acyl chloride is neutralized by hydroxide in the aqueous phase. Because the amide function is generally highly polar and hydrophilic, it shows a great tendency to absorb moisture. Incorporation of these units into the siloxane backbone increases water miscibility causing the polymers to emulsify easily, thus making phase separation difficult. To some extent, this problem can be overcome by using chlorinated solvents such as methylene chloride or chloroform but, unfortunately, such solvents are toxic. Moreover, when larger amounts of amide functionality or more resinous structure or both are used, it becomes very difficult to prepare such compounds using a two-phase system even when chlorinated solvents are used. Finally, because of the presence of the aqueous phase, it is impossible to prepare aminosilanes containing hydrolytically unstable groups using this process.

Varaprath et al in U.S. Pat. No. 4,861,906, issued Aug. 29, 1989, described an improved method for preparing acylamino organosilicon compounds which avoids the phase separation and toxicity problems previously encountered. This method permits use of silane starting materials having hydrolytically unstable groups such as $CH_3OSi$. This method of Varaprath et al comprises reacting an acyl halide with an aminosilicon compound having at least one silicon-bonded amino-substituted hydrocarbon radical containing at least one nitrogen-bonded hydrogen in the presence of a non-aqueous solvent such as toluene or hexane, a metal alkoxide such a sodium methoxide, and a non-aqueous cosolvent for the metal alkoxide such as methanol. This reaction can be carried out at a temperature of from about $-10°$ C. to $+10°$ C. and the weight percent of methanol in a mixture of methanol and sodium methoxide can be about 1 to 25 weight percent. Varaprath et al is hereby incorporated by reference to show this process. Although this method described by Varaprath et al is an excellent method for the preparation of acylamino-organo functional organosilanes and siloxanes certain disadvantages have become apparent when the utility of these compounds are for use in the electronics industry.

Preparation of ultraviolet radiation (UV) curable compositions targeted for use on electronic devices require intermediates which will provide the desired performance. Several key criteria for such applications would include ionic purity, lot-to-lot uniformity, UV cure responsiveness, low temperature capability, thermal stability, resistance to degradation by moisture, and non-corrosivity. The Varaprath et al method is a step toward meeting these requirements, but further improvement is necessary and was thus sought.

SUMMARY OF THE INVENTION

The present invention is an improvement of the non-aqueous method described by Varaprath et al and relates to a method for preparing an organosilicon compound containing at least one silicon-bonded acylamino-substituted hydrocarbon radical comprising reacting an acyl halide with an aminosilicon compound having at least one silicon-bonded amino-substituted hydrocarbon radical containing at least one nitrogen-bonded hydrogen, all other silicon valences therein being satisfied by radicals selected from the group consisting of organic radicals and divalent oxygen atoms, in the presence of a non-aqueous solvent, a metal alkoxide, and a non-aqueous cosolvent for said metal alkoxide, the improvement consisting essentially of mixing the aminosilicon compound which is an amino functional siloxane in the non-aqueous solvent which is a non-polar solvent, adding a non-protic acid acceptor, cooling the resulting mixture to a temperature of from $-5°$ C. to $+5°$ C., then adding the non-aqueous cosolvent which is an alcohol, gradually adding a solution of the acyl halide which is an acryloyl chloride in a non-polar solvent whereupon by-produced salt forms, neutralizing the mixture with a mild base after the addition of the acryloyl halide solution and after the reaction is completed, filtering to remove the by-produced salts, adding a radical scavenger, and vacuum stripping to remove volatiles.

DETAILED DESCRIPTION OF THE PREFERRED EMBODIMENTS

The improvements of the present invention are based on careful control of the reaction conditions and selection of reaction ingredients. The method of the present invention provides for a non-aqueous conversion process of amino functional siloxanes to acrylamide functional siloxanes with a conversion >95%, ionic purities such that the concentrations of sodium and potassium are <2 ppm and chloride <10 ppm, and the viscosity of the starting amino functional siloxane is essentially retained. These improvements are realized by controlling the polarity of the medium by using a non-polar solvent, such as hexane or heptane, controlling the acidity during the reaction to reduce chain scission of the siloxane polymer by adding the alcohol cosolvent after the mixture of amino functional siloxane, non-polar solvent, and non-protic acid acceptor is cooled to a temperature of from $-5°$ C. to $+5°$ C., using limited amounts of the alcohol cosolvent which facilitates the neutralization during the addition of the acryloyl chloride while maintaining the ionic purity of the final product, and using a mild base such as sodium bicarbonate to neutralize to acid numbers of <0.01 mg KOH/g.

The aminosilicon compound is an amino functional siloxane, preferably an aminoalkyl siloxane having at least one silicon-bonded, amino-substituted hydrocarbon radical containing at least one nitrogen-bonded hydrogen. The amino functional siloxane is reacted with an acryloyl halide in a nonaqueous, non-polar, and non-toxic solvent such as hexane or heptane. The silicon-bonded, amino-substituted hydrocarbon radical preferably has the formula $-Q(NHQ')_aNHR''$ wherein Q and Q' are divalent hydrocarbon radicals, R'' is H or a monovalent hydrocarbon radical, and a is 0 or 1. The acryloyl halide preferably has the formula R''' COX where R''' is acryloyl or methacryloyl radical and X is a halogen atom, preferably chlorine.

The non-protic acid acceptor is preferably an alkali metal alkoxide such as sodium methoxide which may be in the form of a dry powder. The non-protic acid acceptor is added to the amino functional siloxane in non-polar solvent and the resulting mixture is cooled to a temperature of from $-5°$ C. to $+5°$ C. before a controlled amount (small amount) of the alcohol cosolvent is added to the mixture. The alcohol cosolvent is preferably methanol and is used to improve the effectiveness of the non-protic acid acceptor to neutralize the HCl that is produced in the primary reaction of amino hydrogen with the acryloyl halide.

The use of nonaqueous solvents allows the use of organosilicon compounds with hydrolytically unstable functional groups such as the methoxy group. Likewise, because no separate aqueous phase is present, there are no phase separation problems. However, improved acrylamide functional siloxanes are obtained when the non-aqueous solvent is a non-polar solvent, such as hexane or heptane and thus the method of this invention is restricted to non-polar solvents.

Thus, an improved method for producing acrylamide functional siloxanes has been found over the method described by Varaprath et al. The acrylamide functional siloxanes are useful in compositions which can be cured by exposure to UV and used in the electronics industry. However, these acrylamide functional siloxanes could also be used in acrylamide functional organosiloxane products useful for paper release coatings. They are also useful as conformal coatings, for example, as moisture and radiation dual cure coatings of the type disclosed in U.S. Pat. No. 4,824,875, issued Apr. 25, 1989 Gutek.

Typically, the amino functional siloxane, the non-polar solvent such as hexane or heptane, and the metal alkoxide such as sodium methoxide are mixed and cooled to a temperature between $-5°$ C. and $+5°$ C., and then a limited amount of the alcohol cosolvent, preferably methanol, is added. The reacting ingredients are agitated throughout the method to ensure that the ingredients remain dispersed throughout the mixture. The acryloyl halide is dissolved in non-polar solvent and the resulting solution is gradually added to the mixture containing the amino functional siloxane. After the addition is complete, the agitation of the resulting mixture is continued until the reaction is complete, for example one hour after the addition is complete. The acryloyl halide, such as acryloyl chloride, reacts with the amine hydrogen to form the acrylamide functionally and by-produce metal halide, such as sodium chloride if acryloyl chloride and sodium methoxide are used. The resulting mixture is further neutralized with a mild base, such as sodium bicarbonate, calcium carbonate, sodium methoxide, pyridine, ion exchange resins, and mixtures thereof. The by-produced metal halide and residual mild base, if it is a salt such as sodium bicarbonate, are removed by filtration and the volaties including the non-polar solvent and volatile mild bases, such as pyridine, are removed by vacuum stripping, i.e. distillation at reduced pressure. The acryloyl halide has the structure R'' COX where X denotes a halogen atom such as I, Cl, Br, or F, preferably chlorine, and R'' denotes an acryloyl or methacryloyl, i.e. the formula are $CH_2=CHC(O)-$ and $CH_2=C(CH_3)C(O)-$ respectively.

The amino functional siloxane that is to be acrylated can have any structure, as long as, it contains at least one silicon atom bonded to an amino-substituted hydrocarbon radical that bears one or more amino radicals at least one of which has a nitrogen-bonded hydrogen atom. The other silicon bonds are satisfied by organic radicals other than amino-substituted hydrocarbon radicals noted above or by silicon-bonded oxygen atoms.

The amino functional siloxane to be acrylated by the process of this invention are preferably siloxanes having the average unit formula $R'_c(R''HN(Q'NH)_aQ)_dSiO_{(4-c-d)/2}$ where R' denotes a monovalent hydrocarbon radical or an alkoxy radical; R'' is a hydrogen atom or an alkyl radical such as methyl, ethyl, propyl, or butyl; a is 0 or 1; c denotes a number having a value of from 0 to <3, such as 0, 0.5, 1.01, 2, 2.1, and 2.95; d denotes a number having a value of from >0 to <3, such as 0.01, 0.5, 1, 2, and 2.95; and c+d has a value of from 1 to 3 such as 1.5, 1.99, 2.01, and 3. Q and Q' are as defined previously. Of course the amino functional siloxane must contain an average of at least one silicon-bonded, amine-substituted hydrocarbon radical per molecule. The siloxanes can contain siloxane units without amino-substituted hydrocarbon radicals such as $R'_cSiO_{(4-c)/2}$ as exemplified by $MeSiO_{3/2}$, $PhSiO_{3/2}$, $PhMeSiO_{2/2}$, $Me_2SiO_{2/2}$, $Me_3SiO_{1/2}$, $Me_2(OMe)SiO_{1/2}$, $ViMe_2SiO_{1/2}$, and $SiO_{4/2}$ units where Me, Ph and Vi denote methyl, phenyl and vinyl, respectively, in addition to siloxane units that contain the required amino-substituted hydrocarbon radicals.

Preferred amino functional siloxanes to be acrylated have the formula YR'$_2$SiO(R$_2$SiO)$_x$(YR'SiO)$_y$SiR'$_2$Y where each Y denotes, independently, an R', —QNHCH$_2$CH$_2$NHR" or —QNHR" radical, at least one Y being an amino-substituted radical, and x and y denote numbers having average values of from 0 to 5000 and 0 to 500, respectively. Examples of preferred amino functional siloxanes to be acrylated by the method of this invention include, but are not limited to,

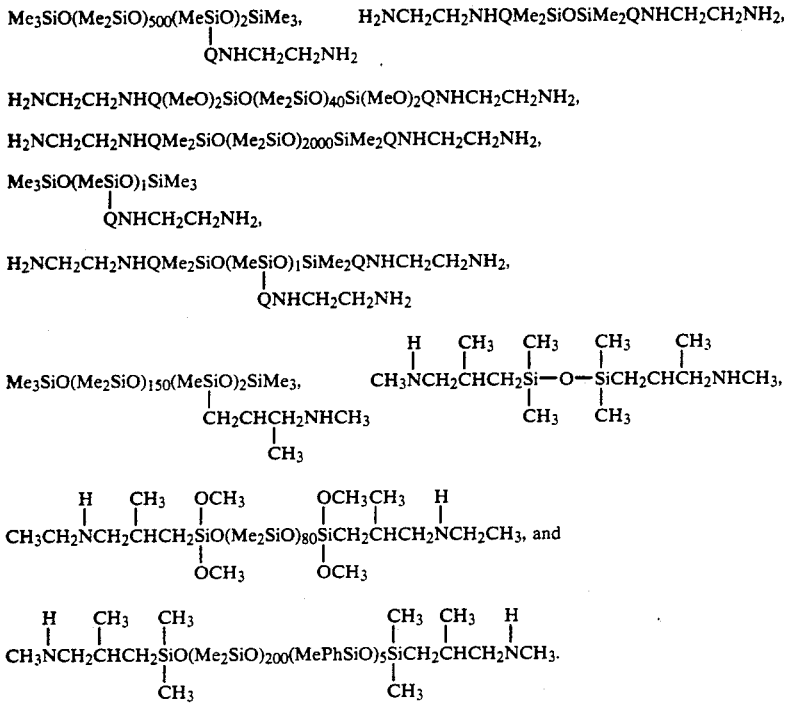

Amino functional siloxanes can also have a cyclic or branched structure such as (YMe$_2$SiO)$_4$Si and (YMeSiO)$_4$, in addition to the linear structures noted above, wherein at least one Y denotes an amino-substituted radical.

Examples of monovalent hydrocarbon radicals, i.e. R radicals, include, but are not limited to, alkyl radicals such as methyl, ethyl, propyl, butyl, hexyl, and octyl; cycloaliphatic radicals such as cyclohexyl; aryl radicals such as phenyl, benzyl, styryl, tolyl, xylyl, and biphenyl (xenyl); halogenated radicals such as —CF$_3$, —CH$_2$CH$_2$CF$_3$, and —C$_6$H$_4$Cl; and alkenyl radicals such as vinyl and allyl. Preferably, R is methyl or phenyl.

Examples of Q radicals and Q' radicals include, but are not limited to, alkylene radicals such as ethylene, propylene, isopropylene, butylene, isobutylene, hexylene, octylene and arylene radicals such as phenylene, and xylylene. Q is preferably isobutylene and Q' is preferably ethylene.

Examples of amino-substituted hydrocarbon radicals include, but are not limited to, NH$_2$CH$_2$CH$_2$CH$_2$—, CH$_3$NHCH$_2$CH$_2$CH$_2$—, NH$_2$CH$_2$CH(CH$_3$)CH$_2$—, NH$_2$CH$_2$CH$_2$NHCH$_2$CH$_2$CH$_2$—, NH$_2$CH$_2$CH$_2$NHCH$_2$CH(CH$_3$)CH$_2$—, NH$_2$(CH$_2$)$_6$NH(CH$_2$)$_3$—, and NH$_2$(CH$_2$)$_6$NHCH$_2$CH(CH$_3$)CH$_2$—.

Silicon-bonded radicals, other than the above-noted amino-substituted hydrocarbon radicals, include organic radicals and silicon-bonded oxygen atoms. R' can be R or alkoxy radicals such as methoxy radical, ethoxy radical, propoxy radical, and butoxy radical. Preferably R' radicals contain no more than 6 carbon atoms, such as methyl, 3,3,3 trifluoropropyl, phenyl and vinyl radicals, and most preferably are methyl or methoxy radicals.

Amino functional siloxanes and their preparation are well known in the organosilicon art. Some are commercially available. The disclosures of U.S. Pat. Nos. 2,557,803, 2,738,357, 2,754,312, 2,762,823, 2,998,406, 3,045,036, 3,087,909, 3,355,424, 3,560,543, 3,890,269, 4,036,868, 4,152,346, and 4,507,455 are incorporated herein by reference to further teach how to prepare amino functional siloxanes that can be used in the method of this invention.

Varaprath et al taught that it was possible to conduct the instant reaction without use of a cosolvent, and that the use of a cosolvent was greatly preferred, because sodium methoxide is essentially insoluble in a solvent such as toluene, and that it was believed to be difficult for the undissolved sodium methoxide to adequately neutralize the amine hydrochloride which was formed as a part of the process, and that unless the amine hydrochloride (formed during the reaction) was neutralized and the amine freed, further reaction with the acyl halide could not take place. Thus Varaprath et al taught the use of a cosolvent system in which the bases were soluble to some extent was necessary to overcomes the apparent problem.

However, not all the problems were solved by Varaprath et al. It was discovered that the presence of the cosolvent, the alcohol, before cooling the mixture of amino functional siloxane, solvent, and metal alkoxide caused the siloxane bonds to rearrange and the original molecular structure of the amino functional siloxane was altered. The present applicants discovered that by adding the alcohol cosolvent after the amino functional siloxane, non-polar solvent, and metal alkoxide was cooled to −5° C. to +5° C. reduced the chain scission of the silicon-oxygen-silicon bonds (rearrangement, i.e. chain scission and siloxane bond formation) and the resulting acrylamide functional siloxane maintained its structure, and as such the viscosity after the acrylamide conversion was essentially the same as amino functional siloxane.

The amount of alcohol cosolvent used is preferably limited for the purpose of reducing the unwanted reaction of it with acryloyl halide, for improving filtration, and reducing the ionics. Regulating the amount of the alcohol, for instance as shown in the examples to follow, to more than about 10 cc methanol per 3,000 grams amino functional siloxane greatly reduces the filtration time. Whereas using amounts of alcohol of about 200 cc methanol per 3,000 grams of amino functional siloxane, increases the amount of ionics in the final product.

The acryloyl halide is added to the amino functional siloxane mixture as a solution in a non-polar solvent, such as hexane or heptane. The non-polar solvent should be one which will not react with the components of the reaction. Preferably the solvent is also a solvent for the organosilicon product of the reaction.

Examples of suitable non-polar solvents include, but are not limited to, hydrocarbons such as hexane, cyclohexane and heptane. Mixtures of two or more solvents can also be used, it only being required that the mixture, and not necessarily all of the components in the mixture, be a solvent for the amino functional siloxane. Preferably solvents such as heptane or hexane are used. The amount of solvent that is used should be sufficient to dissolve the amino functional siloxane and, preferably, the organosilicon product as well.

Since acryloyl chloride reacts with methanol or sodium methoxide to form esters, about 10% excess acryloyl chloride, based on the amine content is preferably used for the reaction. A deficiency of acryloyl halide relative to the total number of reactive amino groups, although merely leading to the preparation of incompletely acrylated product may undergo a Michael-Addition type reaction. For this reason, it is preferred, although not required, to fully acrylate the amino functional siloxane when an acryloyl halide is used. A slightly less than equimolar amount of sodium methoxide to acryloyl chloride are also preferably used so that the solution is maintained as slightly acidic. A large deficiency of sodium methoxide relative to the amount of hydrogen halide produced is to be avoided since an excess of hydrogen halide will inhibit the reaction from going to completion.

This method should be practiced at a temperature of from −5° C. to +5° C., preferably at about 0° C., to minimize the formation of by-products. Reaction temperatures lower than −5° C. might be used because no aqueous phase is present, but they are not practical, and reaction temperatures higher than about +5° C. will substantially reduce the yield of desired product.

During and after the addition of the acryloyl halide component to the amino functional siloxane, the reaction mixture should be thoroughly agitated to maintain an intimate contact between the metal alkoxide and the hydrogen chloride. The usual low shear means such as stirrers, paddles, and impellers are sufficient to maintain sufficient agitation. Agitation is maintained until the acrylation reaction is finished, typically within an hour. After the reaction is finished, the product of the reaction is further neutralized with a mild base. The neutralized product is then filtered to remove the by-produced salts, such as sodium chloride, and any residual mild base, such as sodium bicarbonate. The volatiles should then be removed from the acrylamide functional siloxane. However, because removal of the volatiles is most efficiently done by vacuum stripping, a free radical scavenger is to be added prior to the vacuum stripping. These radical scavengers should be ones which do not introduce ionic substances into the acrylamide product. Such radical scavengers include p-methoxyphenol (MEHQ), phenothiazine, hydroquinone, catechol, 4-t-butylcatechol, 2,6-di-t-butyl-p-methoxyphenol, and N-phenyl-2-naphthylamine. The radical scavengers can be a single compound or mixtures of compounds, and preferably the free radical scavengers are p-methoxyphenol, phenothiazine, or mixtures thereof. After the free radical scavenger is added to the product mixture, the volatiles, namely the non-polar solvent, is removed by vacuum stripping, i.e. distillation at reduced pressure. The pressure should be reduced by an amount which will permit the efficient removal of the volatiles without the necessity of increasing the temperature above a polymerization temperature of the acrylamide functional siloxane.

The products of this method are useful as a reactive component in free radical curable compositions, such as UV radiation curable compositions, such as a component of dual cure systems.

The following examples are presented for illustrative purposes and should not be construed as limiting the present invention which is properly delineated in the claims. In the following examples, "part" and "parts" are "part by weight" and "parts by weight" respectively; and viscosities are at 25° C. unless otherwise stated.

EXAMPLE 1

An amino functional endblocked polydiorganosiloxane was prepared by charging to a reactor 80.98 parts of hydroxyldimethylsiloxy endblocked poly(dimethylsiloxane) having an average of 10 dimethylsiloxane units per molecule and slowly adding 19.02 parts of a silane of the formula

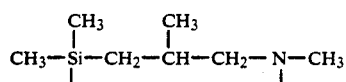

while under a nitrogen blanket and maintaining the temperature below 30° C. After the addition of the silane was completed, the reaction was slowly heated to 80° C. and maintained at that temperature for 1 hour. Volatiles were then removed at 80° C. and about 45 mmHg. The resultant amino functional endblocked polydiorganosiloxane, Amino-Polymer A, had an amine neutral equivalent (ANE) of 708.5 g/equivalent.

An amino functional endblocked polydiorganosiloxane, Amino-Polymer B, was prepared by charging to a reactor 3.76 parts of Amino-Polymer A, 12.64 parts of poly(methylphenylsiloxane) cyclics having from 3 to 6 methylphenylsiloxane units per molecule, 81.92 parts of poly(dimethylsiloxane) cyclics having from 3 to 6 dimethylsiloxane units per molecule, 0.49 part of dimethyl formamide, and 0.01 part of a potassium silanolate catalyst. The resulting mixture was heated at 150° C. for about 8 hours, cooled to 50° C. and then neutralized with 0.044 part of propionic acid. The mixture was stirred for at least one hour, the excess propionic acid was neutralized with 0.049 part of sodium bicarbonate, and then stripped at 150° C. and about 45 mmHg. To the stripped mixture was added 0.99 part of Supercell, a diatomaceous earth filtering aid, and then the mixture was pressure filtered. The resultant amino functional endblocked polydiorganosiloxane, Amino-Polymer B, had an ANE of 17,870 g/equivalent, a refractive index of 1.4245, a viscosity of 6.75 Pa.s, and a non-volatile content of 97.7%.

An acrylamide functional endblocked polydiorganosiloxane was prepared by adding to a 12-liter, 3-necked flask, 3,000 g Amino-Polymer B, 3,000 g heptane, and 12.70 g sodium methoxide. The mixture was cooled to between 0° C. and 5° C. and 76.3 cc methanol was added and then 19.10 cc of acryloyl chloride in 281 cc heptane was added in 2 hours. After about one hour 120 g sodium bicarbonate and 60 g of Supercell were added to neutralize the mixture. After stirring the mixture until it was neutral, it was pressure filtered through a 0.22 micron membrane filter. The resultant clear solution was mixed with 50 ppm p-methoxyphenol (MEHQ) and 25 ppm phenothiazine and vacuum stripped to 50° C. and less than 10 mmHg. The resulting product was an acrylamide functional polyorganosiloxane where the amine groups were converted to acrylamide functionality of the formula

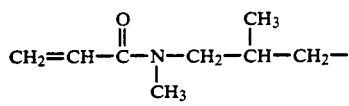

and is designated Acrylamide A which had a 98.3% conversion of amine to acrylamide, a viscosity of 5.44 Pa.s, less than 1 ppm chloride, less than 0.5 ppm sodium, and less than 0.5 ppm potassium.

An ultraviolet radiation curable composition was prepared by mixing 100 parts of Acrylamide A with one part of

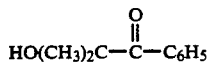

as photosensitizer. The composition was cast onto a glass microslide at 10 mils wet thickness and irradiated with ultraviolet radiation from a UV-6 Single Lamp Conveyorized UV Curing Unit manufactured by Co-light, Minneapolis, Minn. The cast wet film was exposed to a dose of 3.0 J/cm² UV light as measured by an IL 390 Light Bug manufactured by International Light. The power setting of the UV-6 was at 300 watts. After exposure to the 3.0 J/cm² of UV light the UV curable composition was solidified to a tack free elastomer form the top of the cast film to the bottom of the cast film.

Another UV radiation curable composition was prepared by mixing 54.64 parts of Acrylamide A, 1.09 parts of 2-hydroxy-2-methyl-1-phenylpropan-1-one, 0.27 part of tetrabutyltitanate, 36.06 parts of fused silica having an average particle size of 4 microns, 3.85 parts of

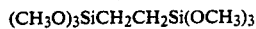

(Alkoxy 1), and 4.09 parts of a reaction product of 11.6 parts of hydroxymethylvinylsiloxy endblocked poly(methylvinylsiloxane) having an average of 10 methylvinylsiloxane units per molecule, 8.4 parts of Alkoxy 1, and 0.2 part of tetrabutyltitanate where the reaction product was made by making a blend of the stated ingredients and then heating at 70° C. for 64 hours (Adhesion Additive 1). The resultant radiation curable composition had a viscosity of 9.2 Pa.s. The composition was stable in one package for more than 3 months and had an opaque white appearance. The ionic purity using a water extraction method was determined and there was less than 1 ppm sodium, less than 1 ppm potassium, and less than 5 ppm chloride. The composition cured to a depth of greater than 100 mils upon irradiation with 4 J/cm² UV light using a Model DRS-120 Ultraviolet Curing System by Fusion Systems Corporation, Rockville, Md. The lamps were set to the highest power level and the UV light measured with an IL-390 Light Bug equipped with a 365 nm filter.

The composition was cast onto Corning 2947 glass microslides and onto aluminum Q-panels with a mill finish, 500-A35. The cast films were cured with 2 J/cm² in the Model DRS-120 Ultraviolet Curing System. The adhesion of the cured films to the substrates was determined by removing it with a spatula. The results were observed after various aging periods at room temperature. The results observed were denoted, AF=adhesive failure; WE=adhesive failure with noticeable adhesion; WD=spotty cohesive failure; and CF=cohesive failure. The observed results were as shown in Table I. In Table I, GL=glass microslide substrate and AL=aluminum Q-panel substrate. The hardness of the cured composition was 20 on the Shore A scale.

TABLE I

| SAMPLE THICKNESS | SUBSTRATE | AMBIENT AGING | | | |
|---|---|---|---|---|---|
| | | 0 MIN | 30 MIN | 120 MIN | 300 MIN |
| 10 mils | GL | CF | CF | CF | CF |
| | AL | AF | AF | AF | CF |
| 20 mils | GL | WE | CF | CF | CF |
| | AL | AF | AF | CF | CF |
| 40 mils | GL | AF | WE | CF | CF |
| | AL | AF | AF | CF | CF |

EXAMPLE 2

An amino functional endblocked polydiorganosiloxane, Amino-polymer C, was prepared as described in Example 1 except the amount of Amino-Polymer A was increased to lower the viscosity. For this polymer, the charge to the reactor was 8.75 parts of Amino-Polymer A, 12.62 parts of poly(methylphenylsiloxane) cyclics having from 3 to 6 methylphenylsiloxane units per molecule, and 76.95 parts of poly(dimethylsiloxane) cyclics having from 3 to 6 dimethylsiloxane units per molecule. The remainder of the reactants and the procedure were the same as for Amino-Polymer B. Amino-Polymer C had an ANE of 7,340 g/equivalent, a viscosity of 0.715 Pa.s, and a non-volatile content of 97.2%.

An acrylamide functional endblocked polydiorganosiloxane was prepared by adding to a 12-liter, 3-necked flask, 3,000 g Amino-Polymer C, 3,000 g heptane, and 23.60 g sodium methoxide. The resulting mixture was cooled to between 0° C. and 5° C. and 10.0 cc methanol was added and then 38.16 cc of acryloyl chloride in 282 cc heptane was added in one hour. The resultant mixture had an acidity of 0.28 mg KOH/g. After about 1 hour, 168 g sodium bicarbonate and 60 g Supercell was added to neutralize the mixture. The mixture was then processed using the procedure above for Acrylamide A. The resulting product, Acrylamide B, had a conversion of 98.9% of amine to acrylamide, a viscosity of 0.8 Pa.s, less than 1 ppm chloride, less than 0.5 ppm sodium, and less than 0.5 ppm potassium.

EXAMPLE 3

Acrylamide functional endblocked polydiorganosiloxanes were prepared from Amino-polymer C using a procedure similar to the procedure in Example 2. Into the 12-liter, 3-necked flask was charged 3,000 g Amino-polymer C, 3,000 g heptane, and sodium methoxide to provide 0.93 equivalents sodium methoxide per equivalent of acryloyl chloride, making a reaction mixture. The reaction mixture was cooled to between 0° C. and 5° C., 50 cc of methanol was added, and then acryloyl chloride in sufficient heptane to give 300 cc solution was gradually added in one hours time to the reaction mixture. After about one hour, about 225 g sodium bicarbonate and 60 g of Supercell (a diatomeous earth) were added to neutralize the mixture. The mixtures were then processed using the procedure for Acrylamide A in Example 1. The results observed upon changing the amount of acryloyl chloride (as shown in Table II) were as in Table II.

using a procedure and reactant concentrations as described in Example 2 except the amount of methanol added to the reaction mixture was varied. the results observed were as shown in Table III.

TABLE III

| METHANOL cc | ADDITION TIME hours | REACTION MIXTURE ACIDITY mg KOH/g | FILTRATION TIME hours | PERCENT CONVERSION | VISCOSITY Pa.S |
| --- | --- | --- | --- | --- | --- |
| 0 | 3 | 0.285 | 40 | 98.9 | 0.71 |
| 10 | 1 | 0.281 | 24 | 98.9 | 0.80 |
| 25 | 1 | 0.391 | 0.8 | 98.9 | 0.65 |
| 50 | 1 | 0.350 | 0.7 | 98.3 | 0.70 |

All resultant acrylamide polymers in Table III had less than 1 ppm chloride, less than 0.5 ppm sodium, and less than 0.5 ppm potassium. Upon admixture with photosensitizer, all acrylamide polymers in Table III were UV curable. The dramatic effect methanol concentration has on filtration time was apparent from this experiment.

EXAMPLE 5

An acrylamide functional endblocked polydiorganosiloxane was prepared from Amino-polymer C using a procedure similar to Example 2. The reaction mixture contained 50.9 cc methanol, sufficient sodium methoxide to provide 0.93 equivalent sodium methoxide per equivalent acryloyl chloride, and acryloyl chloride added gradually over a two hour period providing 1.3 equivalents acryloyl chloride per equivalent of amine. The resulting acrylamide product had a conversion of 98.1% of amine to acrylamide, a viscosity of 0.6 Pa.s, less than 1 ppm chloride, less than 0.5 ppm sodium, and less than 0.5 ppm potassium. An ultraviolet radiation curable composition was prepared by mixing 9.2 parts of the acrylamide product, 0.05 part tetrabutyltitanate, 0.1 part of 2-hydroxy-2-methyl-1-phenyl-propan-1-one, 0.25 part of Alkoxy 1, and 0.5 part of Adhesion Additive 1. Films were cast at 10 mils wet thickness, cured by exposure to UV radiation, and the adhesion measured as described in Example 1. The results observed were as shown in Table IV.

TABLE IV

| SUBSTRATE | AMBIENT AGING | | | | HEAT AGE* |
| --- | --- | --- | --- | --- | --- |
|  | 0 MIN | 60 MIN | 120 MIN | 24 HRS |  |
| SILICON NITRIDE | AF | WE | WE | CF | CF |
| SILICON DIOXIDE | AF | AF | AF | CF | CF |
| EPOXIDE RESIN | WD | CF | CF | CF | CF |
| POLYIMIDE RESIN | WD | WD | WD | CF | CF |
| COPPER | AF | AF | AF | AF | AF |

*HEAT AGE = 20 hours at ambient and 30 minutes at 150° C.

EXAMPLE 6

TABLE II

| POLYMER | ACRYLOYL CHLORIDE | | SODIUM METHOXIDE, g | PERCENT CONVERSION | VISCOSITY Pa.S | Na ppm | K ppm | Cl ppm |
| --- | --- | --- | --- | --- | --- | --- | --- | --- |
|  | cc | eq/eq NH |  |  |  |  |  |  |
| ACRYLAMIDE C | 45.1 | 1.3 | 27.89 | 98.4 | 0.66 | <0.5 | <0.5 | <1.0 |
| ACRYLAMIDE D | 41.6 | 1.2 | 25.74 | 98.4 | 0.68 | " | " | " |
| ACRYLAMIDE E | 38.2 | 1.1 | 23.60 | 98.3 | 0.70 | " | " | " |
| ACRYLAMIDE F | 34.7 | 1.0 | 21.45 | 93.5 | 0.84 | " | " | " |

EXAMPLE 4

Acrylamide functional endblocked polydiorganosiloxanes were prepared from Amino-polymer C An amino functional endblocked polydiorganosiloxane, Amino-polymer D was prepared as described in Example 1 except the amounts were varied to provide 44 mole percent of the siloxy groups being phenyl and 56 mole percent of the siloxy groups being methyl. Amino-polymer D had an average formula

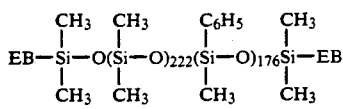

in which EB represents the endblocking in this polymer and was the amino group of the formula

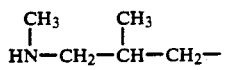

Amino-polymer D had a viscosity of 13.2 Pa.S as measured in accordance with ASTM-D 1084B and an ANE of 23,500 g/eq.

Acrylamide functional endblocked polydiorganosiloxanes were prepared from Amino-polymer D using a procedure similar to that in Example 2. Into the 12-liter, 3-necked flask was charged 3,000 g Amino-polymer D, 3,000 g heptane, and 7.43 g sodium methoxide. The resulting reaction mixture was cooled to between 0° C. and +5° C., 50 cc of methanol was then added, followed by gradually adding 12.42 acryloyl chloride in 263 g heptane. Mixtures were processed as described in Example 2 except that the addition time for the addition of the acryloyl solution was varied as shown in Table V which also shows the observed results.

EXAMPLE 7

Acrylamide functional endblocked polydiorganosiloxanes were prepared from Amino-polymer C using a procedure similar to that in Example 2. Into a 12-liter, 3-necked flask was charged 3,000 g Amino-polymer C, 3,000 g heptane, and sodium methoxide to provide 1.03 equivalents sodium methoxide per equivalent of acryloyl chloride. The reaction mixture was cooled to between 0° C. to +5° C., methanol was added, and then acryloyl chloride in sufficient heptane to provide a 12.6 volume/volume concentration and 1.2 equivalents of acryloyl chloride per equivalent of amine was gradually added in 3.5 hours. The resultant alkaline solutions were neutralized with propionic acid and calcium carbonate and processed using the procedure described for Acrylamide A in Example 1. The results observed upon changing the amount of methanol were as shown in Table VI.

TABLE VI

| POLYMER | METHANOL cc | REACTION MIXTURE ALKALINITY* | PERCENT CONVERSION | VISCOSITY Pa.S | Na ppm | K ppm | Cl ppm |
|---|---|---|---|---|---|---|---|
| ACRYLAMIDE L | 76.3 | 0.00 | 94.8 | 0.41 | 1.2 | <0.5 | <1.0 |
| ACRYLAMIDE M | 200 | 0.014 | 92.6 | 0.58 | 25 | " | " |

*mg KOH/g

Preparation of Acrylamide-M was a comparative example used to demonstrate the effect of high alcohol content on the resulting ionics.

EXAMPLE 8

Acrylamide functional endblocked polydiorganosiloxanes were prepared from Amino-polymer B using a procedure similar to that in Example 2. Into a 12-liter, 3-necked flask was charged 3,000 g Amino-polymer B, 3,000 g heptane, and 12.19 g sodium methoxide. The resulting reaction mixture was cooled to between 0° C. and +5° C., 76.3 cc methanol was added, and then 19.1 cc of acryloyl chloride in 281 cc heptane

TABLE V

| POLYMER | ADDITION TIME minutes | REACTION MIXTURE ACIDITY, mgKOH/g | PERCENT CONVERSION | VISCOSITY Pa.S | Na ppm | K ppm | Cl ppm |
|---|---|---|---|---|---|---|---|
| ACRYLAMIDE H | 6.5 | 0.197 | 98.7 | 17.0 | <0.5 | <0.5 | <1.0 |
| ACRYLAMIDE I | 15 | 0.167 | 98.7 | 16.1 | " | " | " |
| ACRYLAMIDE J | 30 | 0.121 | 98.8 | 15.7 | " | " | " |
| ACRYLAMIDE K | 120 | 0.00 | 92.3 | 19.1 | " | " | " |

An ultraviolet radiation curable composition was prepared by mixing 98 parts of Acrylamide H, 1 part of an 8 weight percent solution of zinc naphthenate solution in mineral spirits, and 1 part of 1-hydroxycyclohexylphenylketone. The resultant composition cured tack free to a 50 Shore OO hardness upon irradiation with 3 J/cm² in the Model DRS-120 Ultraviolet Curing System.

was gradually added in 4 hours. The resultant mixture was split into seven portions 30 minutes after the addition of the acryloyl chloride solution was completed and let set overnight. After measuring the initial acidity of each sample, neutralization agents were added and the resultant mixtures reacted for about 16 hours, then pressure filtered at 40 psi through a 0.22 micron membrane filter, and then vacuum stripped. The results observed upon changing the neutralization agents were as shown in Table VII.

TABLE VII

| POLYMER | NEUTRALIZATION AGENT** | REACTION MIXTURE ACIDITY | | PERCENT CONVERSION | Na ppm | K ppm | Cl ppm |
|---|---|---|---|---|---|---|---|
| | | INITIAL* | AFTER*** | | | | |
| ACRYLAMIDE N | 1 wt % ion exchange resin | 0.0368 | 0.0052 | 97.9 | <0.5 | <0.5 | <0.5 |
| ACRYLAMIDE O | 1 wt % NaHCO₃ | 0.0168 | 0.0083 | 97.8 | " | " | " |
| ACRYLAMIDE P | 1 wt % CaCO₃ | 0.0201 | 0.000 | 98.0 | " | " | " |
| ACRYLAMIDE Q | 0.5 wt % NaHCO₃ + 0.5 wt % CaCO₃ | 0.0330 | 0.000 | 98.0 | " | " | " |

TABLE VII-continued

| POLYMER | NEUTRALIZATION AGENT** | REACTION MIXTURE ACIDITY INITIAL* | REACTION MIXTURE ACIDITY AFTER*** | PERCENT CONVERSION | Na ppm | K ppm | Cl ppm |
|---|---|---|---|---|---|---|---|
| ACRYLAMIDE R | NaOMe**** | 0.0210 | 0.000 | 97.8 | " | " | " |
| ACRYLAMIDE S | Pyridine***** | 0.0249 | 0.000 | 98.1 | " | " | " |
| ACRYLAMIDE T | Pyridine***** | 0.0206 | 0.000 | 97.9 | | | |

*mg KOH/g
**All samples additionally contained 1 wt/wt % Supercell
***After neutralization, mg KOH/g
****0.5 wt % NaHCO$_3$ + 0.5 wt % CaCO$_3$ + sodium methoxide added to provide 0.9 equivalent sodium methoxide per 1 equivalent of acidity.
*****Pyridine added to provide 1 equivalent of pyridine per 1 equivalent of acidity.

EXAMPLE 9

An acrylamide functional endblocked polydiorganosiloxane was prepared as in Example 8 except the amount of sodium methoxide used was 11.81 g. Thirty minutes after the addition of the acryloyl chloride solution was completed, the reaction mixture was separated into two portions and let set overnight. To one portion was added 1 wt/wt % calcium carbonate and 1 wt/wt % Supercell and to the other portion was added 1 wt/wt % sodium bicarbonate and 1 wt/wt % Supercell. These mixtures were agitated and aliquots withdrawn as a function of time to determine acidity and percent conversion. The results were as shown in Table VII.

TABLE VIII

| NEUTRALIZATION TIME, hours | CALCIUM CARBONATE | | SODIUM BICARBONATE | |
|---|---|---|---|---|
| | REACTION MIXTURE ACIDITY, mgKOH/g | PERCENT CONVERSION | REACTION MIXTURE ACIDITY, mgKOH/g | PERCENT CONVERSION |
| 0.0 | 0.0464 | 98.2 | 0.0494 | 98.0 |
| 1.5 | 0.0387 | 98.0 | 0.0244 | 98.0 |
| 3.5 | 0.0439 | 98.1 | 0.0136 | 98.1 |
| 7.5 | 0.0469 | 98.2 | 0.0146 | 97.8 |
| 25.5 | 0.0330 | 98.0 | 0.0048 | 98.1 |

That which is claimed is:

1. In a method for preparing an organosilicon compound containing at least one silicon-bonded acylamino-substituted hydrocarbon radical comprising reacting an acyl halide with an aminosilicon compound having at least one silicon-bonded amino-substituted hydrocarbon radical containing at least one nitrogen-bonded hydrogen, all other silicon valences therein being satisfied by radicals selected from the group consisting of organic radicals and divalent oxygen atoms, in the presence of a non-aqueous solvent, a metal alkoxide, and a non-aqueous cosolvent for said metal alkoxide,
the improvement consisting essentially of mixing the aminosilicon compound which is an amino functional siloxane in the non-aqueous solvent which is a non-polar solvent, adding a non-protic acid acceptor, cooling the resulting mixture to a temperature of from −5° C. to +5° C., then adding the non-aqueous cosolvent which is an alcohol, gradually adding a solution of the acyl halide which is an acryloyl chloride in a non-polar solvent whereupon by-produced salt forms, neutralizing the mixture with a mild base after the addition of the acryloyl halide solution, filter to remove the by-produced salts, adding a radical scavenger, and vacuum strip to remove volatiles.

2. The method according to claim 1 wherein said amino functional siloxane has the formula $$YR'_2SiO(R_2SiO)_x(YR'SiO)_ySiR'_2Y$$

wherein Y denotes R' or

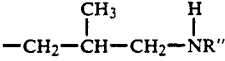

each R' is independently selected from methyl or phenyl, each R is independently selected from methyl or phenyl, R" is a hydrogen atom or an alkyl radical, x has a value of from 0 to 5000, and y has a value of from 0 to 500, where at least one Y is

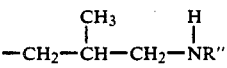

3. The method according to claim 2 in which the amino functional siloxane has the formula

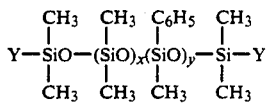

wherein Y has the formula

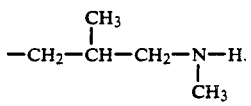

4. The method according to claim 1 in which the non-protic acid acceptor is sodium methoxide, the alcohol cosolvent is methanol, the non-polar solvent is hexane or heptane, the acryloyl halide is acryloyl chloride, and the radical scavenger is a mixture of p-methoxyphenol and phenothiazine.

5. The method according to claim 2 in which the non-protic acid acceptor is sodium methoxide, the alcohol cosolvent is methanol, the non-polar solvent is hexane or heptane, the acryloyl halide is acryloyl chloride, and the radical scavenger is a mixture of p-methoxyphenol and phenothiazine.

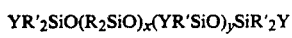

6. The method according to claim 3 in which the non-protic acid acceptor is sodium methoxide, the alcohol cosolvent is methanol, the non-polar solvent is hexane or heptane, the acryloyl halide is acryloyl chloride, and the radical scavenger is a mixture of p-methoxyphenol and phenothiazine.